United States Patent
Berman

[11] Patent Number: 6,017,366
[45] Date of Patent: Jan. 25, 2000

[54] RESORBABLE INTERPOSITION ARTHROPLASTY IMPLANT

[75] Inventor: Andrew B. Berman, Camp Verde, Ariz.

[73] Assignee: W. L. Gore & Associates, Inc., Newark, Del.

[21] Appl. No.: 08/844,486

[22] Filed: Apr. 18, 1997

[51] Int. Cl.$^7$ ............................................. A61F 2/42
[52] U.S. Cl. ......................... 623/21; 623/13; 623/20; 606/77
[58] Field of Search ........................ 623/13, 20, 21, 623/8; 606/77

[56] References Cited

U.S. PATENT DOCUMENTS

| | | |
|---|---|---|
| 3,745,590 | 7/1973 | Stubstad . |
| 3,924,276 | 12/1975 | Eaton . |
| 4,164,793 | 8/1979 | Swanson . |
| 4,198,712 | 4/1980 | Swanson . |
| 4,400,833 | 8/1983 | Kurland ............................ 623/16 |
| 4,411,027 | 10/1983 | Alexander et al. .................. 623/16 |
| 4,429,080 | 1/1984 | Casey et al. . |
| 4,495,664 | 1/1985 | Blanquaert ........................ 623/23 |
| 4,634,445 | 1/1987 | Helal ............................... 623/21 |
| 4,661,536 | 4/1987 | Dorman et al. .................... 523/113 |
| 4,880,429 | 11/1989 | Stone .............................. 623/16 |
| 4,911,718 | 3/1990 | Lee et al. ........................ 623/18 |
| 4,936,860 | 6/1990 | Swanson . |
| 4,955,914 | 9/1990 | Swanson . |
| 4,969,908 | 11/1990 | Swanson . |
| 5,002,583 | 3/1991 | Pitaru et al. . |
| 5,007,934 | 4/1991 | Stone . |
| 5,026,381 | 6/1991 | Li . |
| 5,080,665 | 1/1992 | Jarrett et al. . |
| 5,108,438 | 4/1992 | Stone . |
| 5,116,374 | 5/1992 | Stone . |
| 5,123,925 | 6/1992 | Smestad et al. . |
| 5,171,273 | 12/1992 | Silver et al. . |
| 5,206,028 | 4/1993 | Li . |
| 5,207,712 | 5/1993 | Cohen ............................. 623/21 |
| 5,263,984 | 11/1993 | Li et al. . |
| 5,306,311 | 4/1994 | Stone et al. . |
| 5,458,653 | 10/1995 | Davidson ......................... 623/16 |
| 5,502,092 | 3/1996 | Barrows et al. . |
| 5,514,181 | 5/1996 | Light et al. . |
| 5,522,895 | 6/1996 | Mikos ............................. 623/16 |
| 5,549,690 | 8/1996 | Hollister . |
| 5,595,621 | 1/1997 | Light et al. . |
| 5,735,902 | 4/1998 | Li et al. . |

FOREIGN PATENT DOCUMENTS

| | | |
|---|---|---|
| 241 252 | 10/1987 | European Pat. Off. . |
| 321389 | 6/1989 | European Pat. Off. . |
| 454645 | 10/1991 | European Pat. Off. . |
| 524874 | 1/1993 | European Pat. Off. . |
| 700671 | 3/1996 | European Pat. Off. . |
| 2470583 | 6/1981 | France . |
| 85/00511 | 2/1985 | WIPO . |
| 88/06872 | 9/1988 | WIPO . |
| 90/00060 | 1/1990 | WIPO . |
| 9413227 | 6/1994 | WIPO . |
| 9517861 | 7/1995 | WIPO . |
| 9522359 | 8/1995 | WIPO . |
| 9641596 | 12/1996 | WIPO . |

*Primary Examiner*—Paul B. Prebilic
*Attorney, Agent, or Firm*—Wayne D House

[57] ABSTRACT

A resorbable implant for interposition arthroplasty which is intended to fill a void between two adjacent bone ends, providing a cushion between the bone ends to prevent impingement of the bone ends while providing time for tissue to infiltrate into the space occupied by the implant. It has a protracted resorption time of preferably at least three months to allow time for the proliferation of load-bearing host fibrous tissue in place of the resorbed implant material. The implant preferably is porous with a pore size of greater than about 80 microns in order to enhance infiltration of fibrous tissue. The implant has a modulus in the range of 0.8 to 20 MPa which is soft enough to allow it to conform to surface irregularities of the adjacent bone surfaces while being hard enough to maintain a desired separation between those bones while tissue infiltration replaces the resorbable implant material. The implant may be preformed to the desired shape or alternatively may be formable by the surgeon by methods such as carving with a scalpel. A preferred application for the implant is as a trapezium bone replacement.

16 Claims, 3 Drawing Sheets

RESORBABLE INTERPOSITION ARTHROPLASTY IMPLANT

FIELD OF THE INVENTION

The present invention relates to the field of implantable devices useful for joint repair and in particular to the field of such devices useful as interposition devices for the repair of small joints

BACKGROUND OF THE INVENTION

Arthritis is one of the most prevalent causes of adult impairment with the small joints of the hand and wrist commonly affected. Disability results from the pain produced by the grinding together of adjacent bones whose natural articular surfaces once covered with slippery cartilage have become rough from disease. Interposition arthroplasty is a common procedure where a biologic or synthetic material is interposed between the bones once the degenerated joint surfaces are removed. The interpositional material serves as a cushion to prevent bone to bone contact and to prevent the collapse of the adjacent bones into the surgically created void. One form of the disease, osteoarthritic degeneration of the thumb basal joint (which is also known as the trapeziometacarpal or carpometacarpal (CMC) joint) is particularly prevalent and debilitating, affecting as many as half of all post-menopausal women. The CMC joint is where the saddle-shaped trapezium bone articulates with the first metacarpal bone allowing motion like that of a mechanical universal joint. An arthritic CMC joint becomes painful enough to limit everyday activity such as grasping or pinching. Symptoms can often be treated with physical therapy, rest, splinting or anti-inflammatory medication. If pain persists surgery may be indicated to allow return to activities of normal daily living. Interposition arthroplasty, the most commonly performed surgical procedure for treating CMC arthritis, has been in use since the early 1970's.

Surgical intervention for treatment of CMC arthritis begins with removal of the diseased tissue, usually the entire trapezium bone or a portion thereof. To prevent the collapse of the first metacarpal bone into the space thus created, a wire pin is often used to align the base of the first metacarpal bone with the base of the index metacarpal. The pin serves as a temporary stabilizer. A tendon, such as the palmaris longus or flexor carpi radialis is harvested from the forearm and rolled up, resembling a rolled "anchovy" or jelly-roll. The anchovy is then sutured to prevent unrolling and is interposed between the base of the thumb metacarpal and the scaphoid, the space previously occupied by the trapezium bone. In some cases a suspensionplasty is performed wherein a further piece of tendon is used to tie the base of the thumb metacarpal to the base of the index metacarpal, thereby "suspending" the thumb metacarpal. The wire pin is left in place for about 4 to 6 weeks while healing occurs. It is usually 8 weeks or more before patients are allowed unrestricted activity.

Although the results of tendon interposition are acceptable, there are a number of drawbacks to this procedure. As with any procedure requiring taking a graft, there is additional surgical trauma and morbidity associated with the graft donor site. In many circumstances, there is not enough tendon available from which a graft may be harvested or the quality of the tissue is inadequate. Another major drawback is the amount of time it takes to harvest a tendon graft and prepare it for interpositional placement. Adding a suspensionplasty can also significantly increase operating time. There is evidence that during healing, the tendon grafts weaken and lose structural strength, necessitating the use of pins to help hold the thumb metacarpal in the right position while dense scar forms which will ultimately support the metacarpal.

Prosthetic material has also been used to treat CMC arthritis. One of the most widely used materials has been silicone rubber. Several implant designs have been manufactured from these materials such as the Swanson design (Wright Medical Technology, Inc., Arlington, Tenn.) which was a cylindrical spacer with a long stem fitted into a canal reamed into the metacarpal. Another design of silicone rubber implant was the Ashworth-Blatt Design (Wright Medical Technology Inc., Arlington, Tenn.) which was a button-shaped spacer with a small locating pin. Problems with fracture and dislocation of these implants led to the Stubstad design (U.S. Pat. No. 3,745,590) which incorporated a polyethylene terephthalate or polytetrafluoroethylene fabric mesh for improved strength and to allow tissue ingrowth for fixation to the metacarpal. The Eaton design (U.S. Pat. No. 3,924,276) addressed dislocation with a perforation to allow fixation by attaching a slip of the flexor carpi radialis tendon. All of these silicone rubber devices were subject to dislocation, fracture, abrasion and fatigue which led to the generation of small particles of silicone. The term "silicone synovitis" was coined to describe the chronic inflammatory reaction that resulted from this liberation of silicone particles.

Other implant materials such as titanium were used that would not be susceptible to abrasion and fatigue. These hard implants have failed due to their inability to conform to the intricate contours of the adjacent bones, causing damage to the bones over time.

Many inventors attempted to address the problems associated with hard implants and degradation of silicone implants by designing two piece implants that were intended to reconstruct an articulating joint. Many of the early designs were basically a ball and socket joint on simple stems. More recently Carignan et al (U.S. Pat. No. 4,955,916) disclose a two piece implant featuring a mesh disk for bone ingrowth into the carpal component. Bouchon et al., (U.S. Pat. No. 5,507,822) disclose a two piece design featuring a threaded metacarpal stem that is screwed into position. Hollister et al (U.S. Pat. No. 5,549,690) features a mathematically modeled torus shaped articulating surface that more closely resembles the natural articulating surface. A device with saddle-shaped articulating surfaces allowing rotary circumduction is disclosed by Linscheid et al., (U.S. Pat. 5,405,400). These types of devices have historically met with numerous problems such as loosening, dislocation, difficult implantation technique, and high cost. Additionally, these devices, as with the silicone devices, require a complete range of sizes to allow for patient to patient variability in size and anatomy. More recently, there have been attempts to find alternative materials for interposition arthroplasty. Among them are the use of donor cadaver tissue and the use of porous expanded polytetrafluoroethylene (ePTFE) vascular grafts. Cadaver tissue is used reluctantly due to the possibility of transmission of viral disease. The use of ePTFE vascular grafts gained popularity in the early 1990's after a publication ("GORE-TEX Interpositional Arthroplasty for Trapeziometacarpal Arthritis," Greenberg, J. and Mosher, J., Abstract, American Society for Surgery of the Hand, Toronto, 1990) highlighted excellent early results with the use of a rolled up GORE-TEX Vascular Graft (W. L. Gore and Associates, Inc., Flagstaff, Ariz.). Long-term data, however, indicated that rolled ePTFE vascular grafts were not suitable for this application and were susceptible to abrasion and particulation similar to the silicone implants ("X-Ray Changes After GORE-TEX Interpositional Arthroplasty: Evidence for Particulate Synovitis," Greenberg et al, Abstract, American Academy of Orthopedic Surgeons, 1990). Most patients were asymptomatic even 5 years after surgery and were subjectively very happy with their outcome. A few patients, however, never had relief of preoperative symptoms of pain and swelling, even three months to a year after surgery. In several cases, the ePTFE anchovies were removed and not replaced for fear of a lingering foreign body reaction. An interesting finding was that these patients continued on to a successful outcome with good function and little or no pain. It is hypothesized that during the period in which the anchovy was in place, scar tissue invaded the region providing a scaffold for structural support that was sufficient to allow removal of the anchovy without collapse. It was observed that perhaps the anchovy only served a temporary function, and that beyond three months some other natural mechanism allowed stability and function of the joint.

None of the described prosthetic interposition arthroplasty and CMC joint reconstruction devices have met with an acceptable degree of success. Problems are mostly associated with long-term break-down, loosening, or dislocation. For these reasons tendon interposition with or without suspensionplasty has remained the gold standard even despite the inherent problems associated with tissue graft harvesting and protracted operating room time.

The present invention relates to a resorbable interposition arthroplasty implant that provides improved performance in comparison to prior devices. Various other implantable orthopedic devices made from resorbable materials have been described. These consist primarily of devices such as plates, pins and screws for bone repair and various devices for the repair and replacement of tendons and ligaments. These devices, particularly those intended for the repair and replacement of tendons and ligaments, are designed to hold the adjacent ends of the adjacent bones of a particular joint in appropriate relationship while accommodating tensile loads, that is, they prevent further separation of the adjacent bone ends during use of the joint. For example, U.S. Pat. Nos. 5,514,181 and 5,595,621 describe elongated bioabsorbable ligaments and tendons in the form of a multilayered spiral roll of a three layer laminate of a foraminous layer, a film layer and a sponge layer. The described devices are intended to provide articles of high tensile strength along their longitudinal axes about which the spiral roll has been formed. The film layer serves to block cellular migration in radial directions inside the prosthesis.

An improved interposition arthroplasty material should provide enough mechanical integrity to allow effective maintenance of the space between the adjacent ends of adjacent bones, preventing impingement of those adjacent bone ends while enhancing the invasion of host scar tissue into the space thereby creating stability. As host scar tissue proliferates, the material would slowly resorb, eventually transferring load-bearing function entirely to the tissue. The material would be simple to use and eliminate the need to harvest autologous tissue while allowing an expedited surgical procedure and avoiding harvest site morbidity and long-term complications due to prosthetic breakdown.

SUMMARY OF THE INVENTION

The present invention provides an implant for interposition arthroplasty which comprises non-autologous, resorbable material. It is proportioned appropriately to be inserted between adjacent ends of adjacent bones, having suitable dimensions and having surfaces contoured appropriately to accommodate the adjacent ends of the adjacent bones so as to prevent impingement of those adjacent bone ends for a period of time adequate to allow the proliferation of load bearing tissue into the space originally occupied by the implant at the time of implantation. The preferred use of the implant is as a replacement for the trapezium bone of a human hand. The implant is useful for the repair of joints of the extremities, meaning joints of the arms or legs particularly including the hands and feet. The implant has a protracted resorbtion time of preferably at least 3 months and up to about 24 months in order to allow time for the proliferation of load-bearing host fibrous tissue. It is open to cellular migration at a relatively uniform rate through the implant, meaning that it does not provide barriers to the migration of cells into the implant in any direction. The implant preferably is porous, having a preferred pore size of greater than about 30 microns and more preferably greater than about 80 microns in order to enhance infiltration of fibrous tissue. The implant is compliant in order to be able to cushion the adjacent ends of adjacent bones thereby preventing impingement of the adjacent bone ends; preferably the implant has a modulus in the range of 0.8 to 20 MPa. The implant preferably has a thickness of at least about 1 mm and more preferably at least about 3 mm in the interest of preventing impingement of the adjacent bone ends. It is anticipated that minimum dimensions for the implant will be on the order of about 5 mm by 5 mm by 1 mm thick; an implant of these approximate dimensions is anticipated to be useful at various different locations in the body such as in the finger joints. A typical trapezium bone is in the range of about 10 mm by 15 mm by 10 mm thick although they can be quite variable. Thickness is taken to be in the direction of the primary (typically the largest) compressive force applied to the implant during normal use.

DETAILED DESCRIPTION OF THE INVENTION

Figure 1:
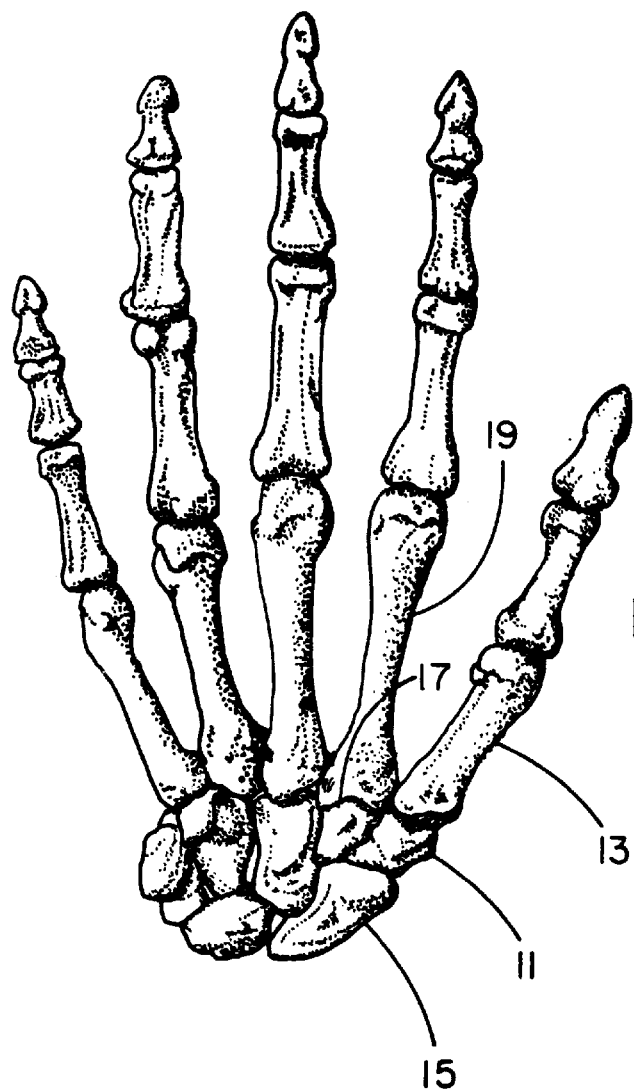
FIG. 1 is an overview of the anatomy of the hand.
Figure 1A:
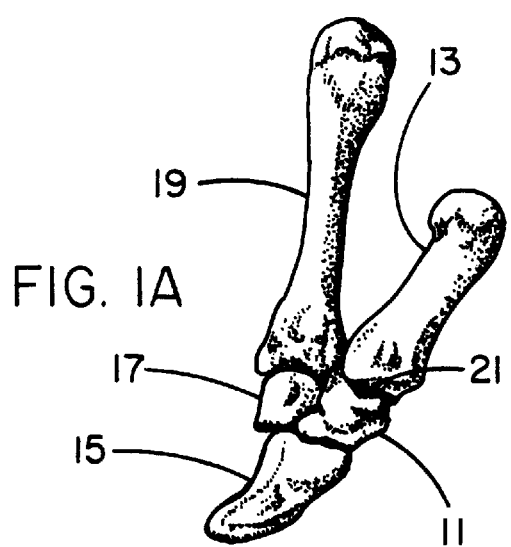
FIG. 1A describes a close up view of the carpometacarpal joint.

FIG. 1 is an overview of the bony anatomy of the human hand while FIG. 1A shows an enlarged view of the first carpometacarpal joint. As described by both of these figures, trapezium 11 articulates directly with the first metacarpal 13 which is the largest bone of the thumb. The trapezium 11 can be seen to have articulating surfaces which come in contact with the first metacarpal 13, scaphoid 15, trapezoid 17 and second metacarpal 19. It can be appreciated from FIG. 1A that the trapezium 11 is a complex shape with distal surface 21 (that articulates with the first metacarpal 13) being saddle-shaped to allow a high degree of mobility of the thumb.

Figure 2:
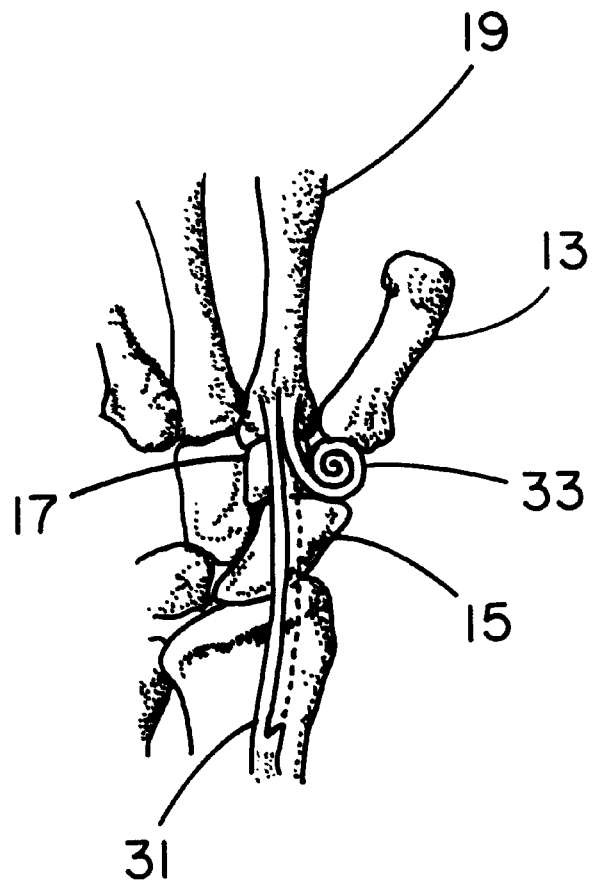
FIG. 2 shows a view of a tendon interposition repair procedure of the prior art.

When the articulating surfaces of the trapezium are destroyed through disease or trauma, the bone is often removed and a tendon interposition is performed as illustrated in FIG. 2. Tendon interposition arthroplasty most often uses the flexor carpi radialis tendon 31. The autologous tendon 31 is split longitudinally as shown so that there is still some functioning tendon left intact. Half of the tendon is cut loose in the forearm, rolled up to create an "anchovy" 33 and placed in the space once occupied by the trapezium 11. The anchovy is often sutured in place to prevent migration. Although the illustration shows the use of the flexor carpi radialis other tendons such as the palmaris longus are also used.

Figure 3:
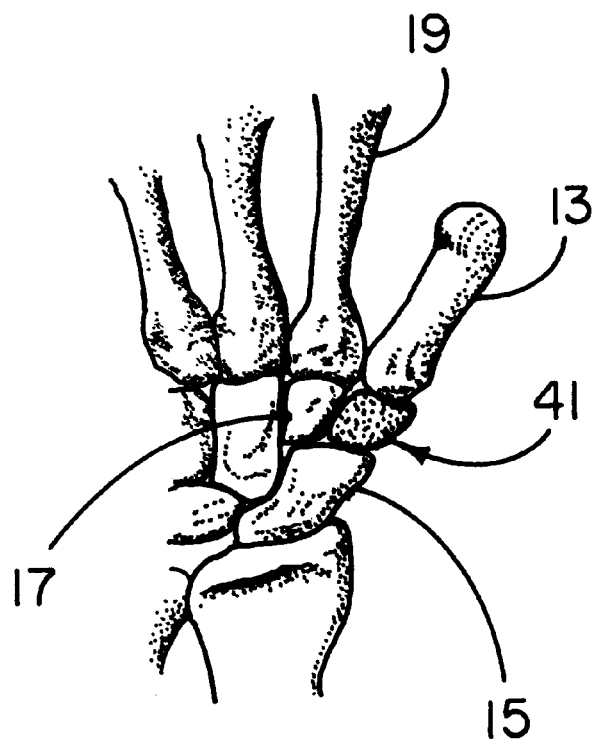
FIG. 3 illustrates a view of the resorbable interposition arthroplasty implant of the present invention showing the implant in position as a replacement for the trapezium bone of the hand.

FIG. 3 describes an interposition arthroplasty procedure according to the present invention. The surgical procedure is similar to that for the conventional tendon arthroplasty procedure shown by FIG. 2 except that no tendon graft is harvested. After removal of the trapezium bone 11, resorbable, non-autologous implant material is provided, proportioned to roughly fit the space previously occupied by the trapezium 11. The proportioned resorbable implant 41 may be provided in a size and shape roughly similar to the native trapezium or optionally can be carved to the desired shape by the medical practitioner to accommodate the surfaces of the first metacarpal 13, the scaphoid 15, the trapezoid 17 and the second metacarpal 19. Because the material of the resorbable implant 41 is conformable due to its inherent compliance, any slight mismatch between the relative shapes of the implant and the adjacent bone surfaces will be accommodated as the implant 41 compresses locally to conform as necessary without causing damage to either the implant or the corresponding adjacent bone surfaces. This conformability allows the implant to accommodate to a substantial extent the variable bone shapes of different individuals.

Carvability of implantable materials is taught by either WO 95/22359 or U.S. Pat. No. 5,098,779.

It is believed that the modulus of the implant should be between about 0.8 and 20 MPa. A modulus of 0.8 MPa is anticipated to provide adequate support between the first metacarpal and scaphoid bones for a period of about ten weeks following implantation. Typically, the entire CMC joint is immobilized for the first six weeks following surgery of the type necessary for implantation of an interposition device of the present invention; the weakened hand is usually capable of only generating about a 0.5 kg pinching force between the tips of their index finger and thumb at ten weeks after surgery. A normal hand by comparison is typically capable of a pinching force of about 2.0 kg. The Young's modulus for cancellous bone is generally reported to be in the range of about 10 to 20 MPa; it is anticipated that the implant should be no harder than these values. A more preferred range is therefore believed to be 0.8 to 10 MPa with 0.8 to about 3 MPa believed to be even more preferred. Generally, rigid implants of materials such as hydroxyapatite, calcium phosphate, calcium sulfate, coral and ceramics are considered to be non-compliant and therefore beyond the scope of the present invention.

The resorbable implant of the present invention may be made of various known resorbable materials in either solid (non-porous) or in porous forms. To achieve the desired conformability, a porous material is preferred. The porosity may take various forms, that is, the implant may be cast or otherwise manufactured to have a conventional porous form such as an open-cell foam structure. A preferred mean pore size is anticipated to be about 80 microns in order to expedite tissue infiltration into the void spaces of the material as it first begins to resorb. Alternatively, the porosity may result from providing the implant in the form of a mat of fibers such as a felt-like form. Such a felt-like form may be manufactured in flat sheet form which may subsequently be rolled up to provide the necessary "anchovy" shape. The individual adjacent fibers may be bonded together or unattached, although the mechanical integrity of the implant is increased if the fibers are attached. The fibers may be of various lengths and diameters; they may be as large in diameter as about 100 microns. This would allow the possibility of forming the fibrous implant from a bundle or wad of small diameter resorbable suture material. Likewise, in order to be shapeable by the surgeon the material should be carvable with a scalpel or other sharp blade.

Resorbable materials useful for the implant include copolymers of lactic acid and glycolic acid (PLA/PGA) adjusted in the desired ratio to achieve the desired rate of resorption. Other potentially useful resorbable materials include polydiaoxanone (PDS), polyhydroxybutyrate, copolymers of hydroxybutyrate and hydroxyvalerate, copolymers of lactic acid and ε-caprolactone, oxidized regenerated cellulose and various forms of collagen. A most preferred material is polyglycolide: trimethylene carbonate tri-block copolymer (PGA:TMC). This material has a history of use as resorbable sutures; it is described in detail by U.S. Pat. No. 4,429,080. The proportions of this or any other selected copolymer or blends of polymers may be adjusted to achieve the desired resorption rate. Other potentially useful resorbable, non-autologous materials including porous forms are described by U.S. Pat. Nos. 4,243,775; 4,300,565; 5,080,665; 5,502,092; 5,514,181 and 5,559,621, and published PCT application WO 90/00060. Various methods of adjusting the rate of resorption of these various materials are known to those skilled in the art of resorbable materials.

Figure 4:
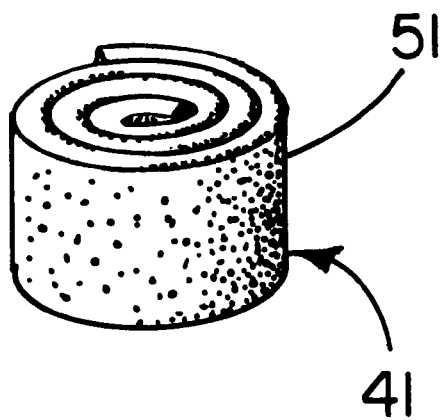
FIG. 4 describes a perspective view of an implant of the present invention formed by spirally rolling a strip of resorbable material to form a jelly roll or "anchovy."

FIG. 4 shows an alternative embodiment wherein the resorbable implant 41 is fabricated from a strip of resorbable material rolled up in spiral or jelly-roll fashion to form an anchovy 51.

Figure 5:
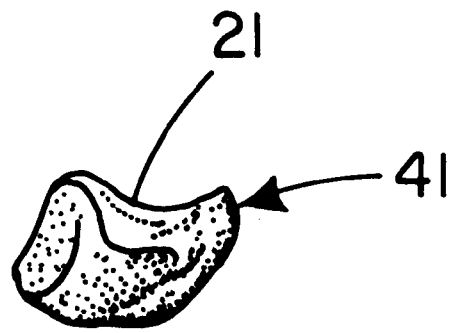
FIG. 5 is a perspective view of a preformed implant shaped like a trapezium bone.
Figure 6:
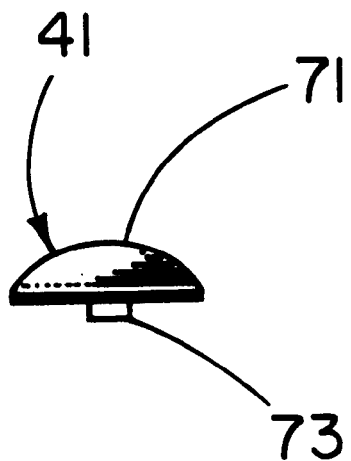
FIG. 6 provides a side view of a preformed implant having a button-like shape.

FIG. 5 describes an alternative embodiment of the present invention wherein the implant 41 is preformed to a specific desired shape such as the shape of the natural trapezium 11 including saddle-shaped surface 21. FIG. 6 describes an alternative embodiment for use when a preformed shape is desired for use when only a partial resection of the trapezium is required. In this embodiment the implant 41 has a generally button-shape 71 and has an integral fixation pin 73 which can be located in a pre-drilled hole located in the unresected portion of the trapezium.

Figure 7:
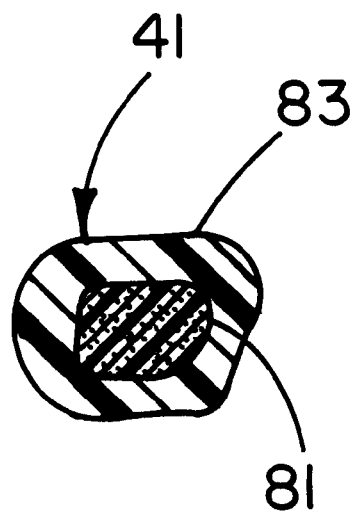
FIG. 7 is a view of an implant having a resorbable outer surface encircling a nonresorbable core.

FIG. 7 shows a cross sectional view of an alternative embodiment wherein a combination of resorbable and a non-resorbable material may be desired for interposition arthroplasty. According to this embodiment, a non-resorbable material such as ePTFE or another biocompatible material is shaped to provide a core 81 upon which is molded a resorbable material thereby forming a resorbable shell 83.

The present invention applies not only to interposition arthroplasty of the thumb carpometacarpal joint but also to other anatomical sites where the interposition of an implantable cushion between two bones is appropriate. An example would be treatment of trauma induced ankylosis of the proximal interphalangeal joint wherein an injury resulted in the fusing of the middle and proximal phalanges. Interposition arthroplasty would be a suitable treatment wherein the connecting hard tissue would be removed and the resorbable implant would be inserted in the resulting void to provide a cushion and a scaffold that would prevent bone to bone contact and allow ingress of host tissue. Other anatomical sites may include but are not limited to the other carpal bones, wrist, and elbow as well as the small joints of the foot.

While the principles of the invention have been made clear in the illustrative embodiments set forth above, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

I claim:

1. An implantable medical device comprising a structural article proportioned to be inserted between adjacent ends of adjacent bones of a hand or foot, the structural article being sufficiently compliant to cushion the adjacent ends of the adjacent bones thereby preventing impingement of adjacent ends, wherein the structural article has a non-resorbable core provided with a resorbable shell and wherein the resorbable shell of the structural article is adapted to be resorbed by a living body over a period of approximately 3 to 24 months.

2. A device according to claim 1 wherein the device is proportioned to replace a trapezium bone.

3. A device according to claim 1 wherein the resorbable material is porous.

4. A device according to claim 3 wherein the resorbable material has a mean pore size of at least about 30 microns.

5. A device according to claim 4 wherein the resorbable material has a mean pore size of at least about 80 microns.

6. A device according to claim 1 wherein the implantable device has a modulus between about 0.8 and 10 MPa.

7. A device according to claim 6 wherein the implantable device has a modulus between about 0.8 and 3 MPa.

8. A device according to claim 1 wherein the implantable device is carvable to a desired shape.

9. A device according to claim 1 wherein the article has a thickness of at least 1 mm.

10. A device according to claim 9 wherein the article has a thickness of at least 3 mm.

11. A method of using a resorbable material for interposition arthroplasty, comprising:

a.) surgically exposing a joint between two bones of a hand or foot;

b.) placing an implant into a space between adjacent ends of two bones wherein the implant comprises a non-resorbable core provided with a resorbable shell wherein the implant is sufficiently compliant to cushion the adjacent ends of the two bones thereby preventing impingement of the adjacent ends; and c.) surgically closing the joint.

12. A method according to claim 11 wherein said joint is a carpometacarpal joint.

13. A method according to claim 11 wherein the resorbable material has a modulus between about 0.8 and 20 MPa.

14. A device according to claim 1 wherein the implantable device has a modulus between about 0.8 and 20 MPa.

15. A device according to claim 14 wherein the resorbable material is porous.

16. A device according to claim 1 wherein the non-resorbable material comprises porous polytetrafluoroethylene.

* * * * *